United States Patent [19]

Allen et al.

[11] Patent Number: 4,912,529
[45] Date of Patent: Mar. 27, 1990

[54] APPARATUS AND METHOD TO COMPENSATE FOR REFRACTION OF RADIATION

[75] Inventors: Gary R. Allen, Georgetown; Philip E. Moskowitz, Peabody, both of Mass.

[73] Assignee: GTE Products Corporation, Danvers, Mass.

[21] Appl. No.: 83,744

[22] Filed: Aug. 7, 1987

[51] Int. Cl.$^4$ .................... G01N 21/00; G01N 21/90
[52] U.S. Cl. .................................. 356/240; 356/246; 356/432
[58] Field of Search ............... 356/240, 246, 319, 337, 356/338, 410, 432

[56] References Cited

U.S. PATENT DOCUMENTS 3,523,738  8/1970  Chisholm ........................... 356/246
4,680,977  7/1987  Conero et al. ...................... 356/338

OTHER PUBLICATIONS

Van Den Hoer, "Diagnostic Methods in Lamp Research," Philips Journal Res., 1983, pp. 188–213.

Primary Examiner—Vincent P. McGraw
Assistant Examiner—S. A. Turner
Attorney, Agent, or Firm—Martha Ann Finnegan

[57] ABSTRACT

An apparatus to compensate for refraction of radiation passing through a curved wall of an article is provided. The apparatus of a preferred embodiment is particularly advantageous for use in arc tube discharge diagnostics. The apparatus of the preferred embodiment includes means for pre-refracting radiation on a predetermined path by an amount equal and inverse to refraction which occurs when radiation passes through a first wall of the arc tube such that, when the radiation passes through the first wall of the arc tube and into the cavity thereof, the radiation passes through the cavity approximately on the predetermined path; means for releasably holding the article such that the radiation passes through the cavity thereof; and means for post-refracting radiation emerging from a point of the arc tube opposite its point of entry by an amount equal and inverse to refraction which occurs when radiation emerges from the arc tube. In one embodiment the means for pre-refracting radiation includes a first half tube comprising a longitudinally bisected tube obtained from a tube which is approximately identical to the arc tube's cylindrical portion and a first cylindrical lens, the first half tube being mounted with its concave side facing the radiation source and the first cylindrical lens being mounted between the first half tube and the arc tube and the means for post-refracting radiation includes a second half tube comprising a longitudinally bisected tube obtained from a tube which is approximately identical to the arc tube's cylindrical portion and a second cylindrical lens, the second half tube being mounted with its convex side facing the radiation source and the second cylindrical lens being mounted between the arc tube and the second half tube. Methods to compensate for refraction of radiation passing into and out of an arc tube is also provided.

11 Claims, 3 Drawing Sheets

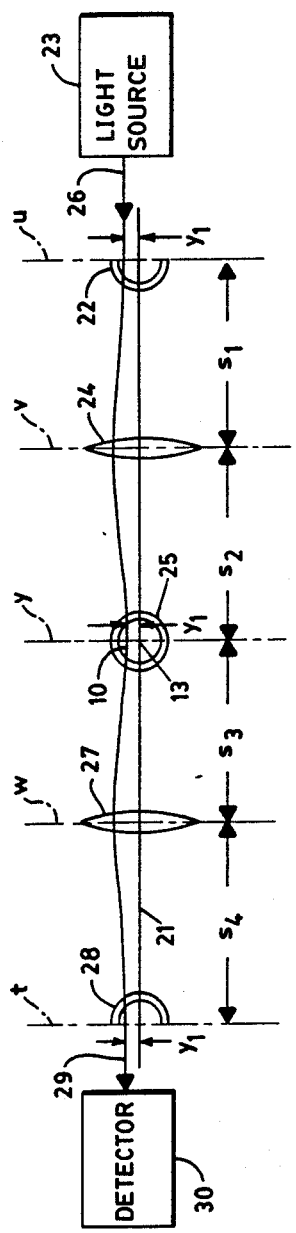
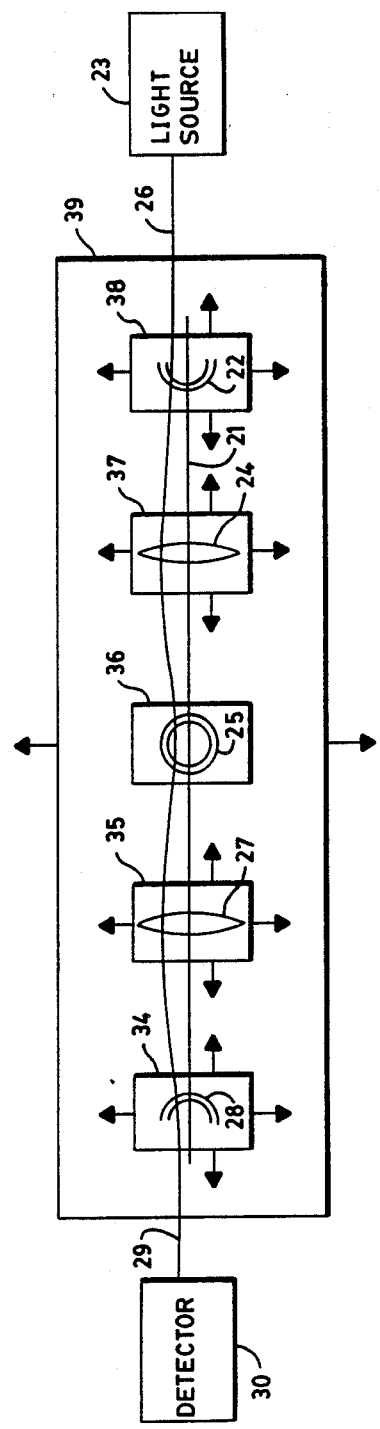
FIG. 2
FIG. 3

APPARATUS AND METHOD TO COMPENSATE FOR REFRACTION OF RADIATION

The Government has rights to this invention pursuant to Contract DE-ACO3-84SF-12235 awarded by the Department of Energy.

TECHNICAL FIELD OF THE INVENTION

The present invention relates to optics and more particularly to an apparatus to compensate for optical refraction.

BACKGROUND OF THE INVENTION

In various types of applications the contents of an optically transparent article with curved walls, such as, for example, a cylindrical tube of glass or quartz, may be diagnosed or analyzed by inspection of radiation emitted from or transmitted through the contents of the article. In passing through the curved walls of the article, however, the path of the radiation is distorted by, e.g., refraction. Such refraction causes the path of the radiation passing through the contents of the article to differ from the intended and expected path. The refraction of the ray is more pronounced as the position of the ray approaches being tangential to the inner wall of the article. Such effects create problems in applications, such as, for example, the diagnosis of light emitted from discharge lamp arc tubes, and the diagnosis of laser beams transmitted through or scattered by arc discharges. Similar problems may exist in commercially-available analytical devices which involve passing a beam of radiation through a sample holder having curved walls such as in, e.g., atomic absorption spectrometers.

The problem of refraction has been particularly troublesome in laser diagnostic techniques which attempt measurements near the inner wall of a discharge lamp arc tube.

One approach for minimizing the refraction problem in arc discharge diagnostics involves moving the detector to intercept the ray along its emergent path. B. Weber, "Mapping of Mercury and Xenon Densities in High Pressure Lamps", 4th Int'l. Symp. on the Sci. and Techn. of Light Sources, Paper No. 1, Karlsruhe, F. R. Germany (April 1986).

This technique, however, is unsatisfactory for rays nearly tangential to the inner wall of the sample vessel. This technique is further not suitable for use in applications which require the light ray to follow an undeviated path through the sample. One example of an application with such requirement involves two intersecting laser beams which must be kept aligned inside the sample as one or both beams is scanned laterally relative to the sample.

The deviation of the light ray path through a sample is especially undesirable in techniques where light scattered from a light beam source or laser is to be detected as the light or laser beam position is scanned through the sample. See, for example, W. J. van den Hoek, Philips J. Res. 38, 188–213 (1983).

SUMMARY OF THE INVENTION

In accordance with one aspect of the present invention there is provided an apparatus to compensate for refraction of radiation passing through a curved wall of an article. The apparatus comprises means for refracting radiation by an amount equal and opposite to refraction which occurs when radiation passes through the curved wall of the article such that refraction of radiation caused by passing through the curved wall of the article is cancelled; and means for releasably holding the article.

In accordance with another aspect of the present invention, there is provided an apparatus to compensate for refraction of radiation passing through an article having curved walls defining a cavity. The apparatus includes means for pre-refracting radiation on a predetermined path by an amount equal and inverse to refraction which occurs when radiation passes through a first wall of the article such that, when the radiation passes through the first wall of the article and into the cavity thereof, the radiation passes through the cavity approximately on the predetermined path; means for releasably holding the article such that the radiation passes through the cavity thereof; and means for post-refracting radiation emerging from a point of the article opposite its point of entry by an amount equal and inverse to refraction which occurs when radiation emerges from the article.

In accordance with still another aspect of the present invention there is provided a method to compensate for refraction of radiation passing into an article having curved walls defining a cavity, the walls of which refract radiation passing therethrough. The method of the present invention comprises pre-refracting radiation traveling on a predetermined path by an amount approximately equal and inverse to refraction occurring when the radiation passes through a first wall thereof, passing the pre-refracted radiation through the first wall of the article and into the cavity thereof, the first wall cancelling the pre-refraction such that the radiation passes through the cavity of the article on the predetermined path. The method may further comprise post-refracting the radiation emerging from the article by an amount approximately equal and inverse to the refraction occurring when radiation on a predetermined path passes through a second wall of the article, thereby providing a light output on the predetermined path.

In accordance with yet another aspect of the present invention there is provided a method to compensate for refraction of radiation passing out of an article having curved walls defining a cavity, the walls of which refract radiation passing therethrough. The method of the present invention comprises refracting radiation emerging from a wall of the article by an amount approximately equal and inverse to refraction occurring when radiation on a predetermined path passes through the wall of the article such that refraction of the radiation caused when the radiation passed through the wall of the article is cancelled.

BRIEF DESCRIPTION OF THE DRAWINGS

In the drawings,

FIG. 1b illustrates a cross-sectional view of the cylindrical portion of the discharge lamp arc tube shown in FIG. 1a;

FIG. 2 schematically illustrates the top view of a preferred embodiment of the apparatus of the present invention in cross-section (not showing the support means), and FIG. 3 schematically illustrates the top view of a preferred embodiment of the apparatus of a preferred embodiment of the present invention in cross-section.

Figure 1A:
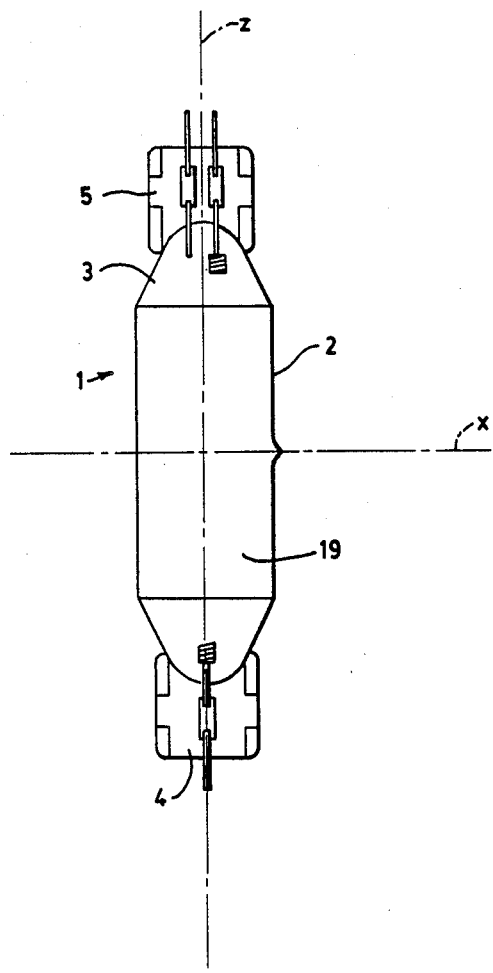
FIG. 1a illustrates a typical discharge lamp arc tube which is an example of an article for which a preferred embodiment of the present invention is adapted.

For a better understanding of the present invention, together with other and further objects, features, advantages, and capabilities thereof, reference is made to the following discussion and appended Claims in connection with the above-described drawings.

DETAILED DESCRIPTION

The present invention is directed to an apparatus and method to compensate for the refraction of radiation which occurs when radiation passes through a curved optically transparent wall.

The apparatus of the present invention is particularly advantageous for use with an optically transparent article having curved walls which define a cavity. The walls of the article refract radiation passing therethrough. The article may be closed at both ends, open at both ends; or closed at one end and open at the other end.

The apparatus of the present invention compensates for refraction of radiation occurring when the radiation passes through a wall of the article. The apparatus is useful when externally generated light is directed into or through an article in carrying out various diagnostic techniques. The apparatus is also useful when light is internally generated within the article and emission diagnostics are called for.

In applications involving, e.g., light scattering or cross beam pumping, the apparatus is used with an external light source which generates a beam of light which is directed through the apparatus having an article mounted therein. In such application, the apparatus is oriented such that the refracting means is interposed between the light source and the article such that the apparatus delivers radiation into the cavity of the article such that the radiation is on approximately the same predetermined path within the cavity as it was prior to its entering the apparatus.

In another application, e.g., emission detection, light is generated within the article while mounted in the apparatus and the emissions are analyzed by a detector. When used with a detector, the apparatus is oriented such that the refracting means is interposed between the article and the detector such that the apparatus delivers the emissions to the detector on approximately the same predetermined path as the emissions within the cavity of the article.

The apparatus of the present invention includes means for refracting radiation by an amount equal and inverse to refraction which occurs when radiation passes through a wall of the article such that refraction of radiation caused by radiation passing through a wall of the article is cancelled. A preferred refracting means includes a compensating means for refracting the radiation by an amount equal to that which occurs when radiation passes through a wall of the article to form compensated radiation, e.g., a hemi-article prepared from an approximately identical copy of the article which is bisected along its longitudinal axis to create two hemi-articles whose curvature, thickness, and refractive indices are identical to those of the article, and means for inverting the compensated radiation, e.g., a lens with its principal plane parallel to the longitudinal axis of the article.

The apparatus further includes means for releasably holding the article in a position in which radiation passing into or out of the cavity of the article passes through the refracting means such that the refracting means cancels the refraction of the radiation which occurs when radiation passes through the wall of the article.

In another embodiment, the apparatus is adapted for use with both a light source and detector and compensates for refraction of radiation occurring both when radiation passes into and out of an article having curved walls defining a cavity. The apparatus of the preferred embodiment includes means for pre-refracting radiation on a predetermined path by an amount equal and opposite to refraction which occurs when radiation passes through a first wall of the article such that, when the radiation passes through the first wall of the article and into the cavity thereof, the radiation passes through the cavity approximately on the predetermined path; means for releasably holding the article such that the radiation passes through the cavity thereof; and means for post-refracting the radiation emerging from a point of the article opposite its point of entry by an amount equal and opposite to refraction which occurs when the radiation emerges from the article.

The apparatus of the present invention is particularly advantageous for use with diagnostic techniques which involve passing one or more laser beams through the contents of a discharge lamp arc tube. Discharge lamp arc tubes typically are fabricated from glass or quartz and have curved walls which define the arc tube cavity. The arc tube cavity is usually of circular cross-section but may have an arbitrarily shaped cross-section. When a laser beam passes through a curved wall of the arc tube, the curvature refracts the laser beam. The refraction causes a deviation of the path of the beam through the cavity of the arc tube. When the beam passes out of the arc tube cavity and through the opposite arc tube wall, the passage through the opposite curved arc tube wall further refracts the beam. The refraction of the beam caused by passing through the arc tube walls upon entry and exit produces inaccuracies and alignment and detection difficulties in diagnostic measurements made using the laser beam(s).

One example of a discharge lamp arch tube typically used in high intensity type discharge lamps of the metal halide type is shown in FIG. 1a. Referring to FIG. 1a with more particularity there is shown an arc tube 1 including a sealed light transmissive envelope 3. The envelope 3 includes pinched sealed portions 4 and 5 at each end thereof and a major cylindrical or tubular portion 2. Preferably the cylindrical portion 2 is of approximately circular cross-section. Inside the hermetically sealed envelope 3, there is a volume 19 in which a fill is present. The fill is volatilized during operation of the lamp. The arc tube has a longitudinal axis, z, which passes through the center of the arc tube envelope 13. An equatorial x-axis is also shown. The x-axis is perpendicular to the longitudinal z axis and passes through the cylindrical portion 2 of the arc tube envelope 3 coincident with the diameter thereof at a point which is approximately the mid point of the length of the arc tube envelope.

Figure 1B:
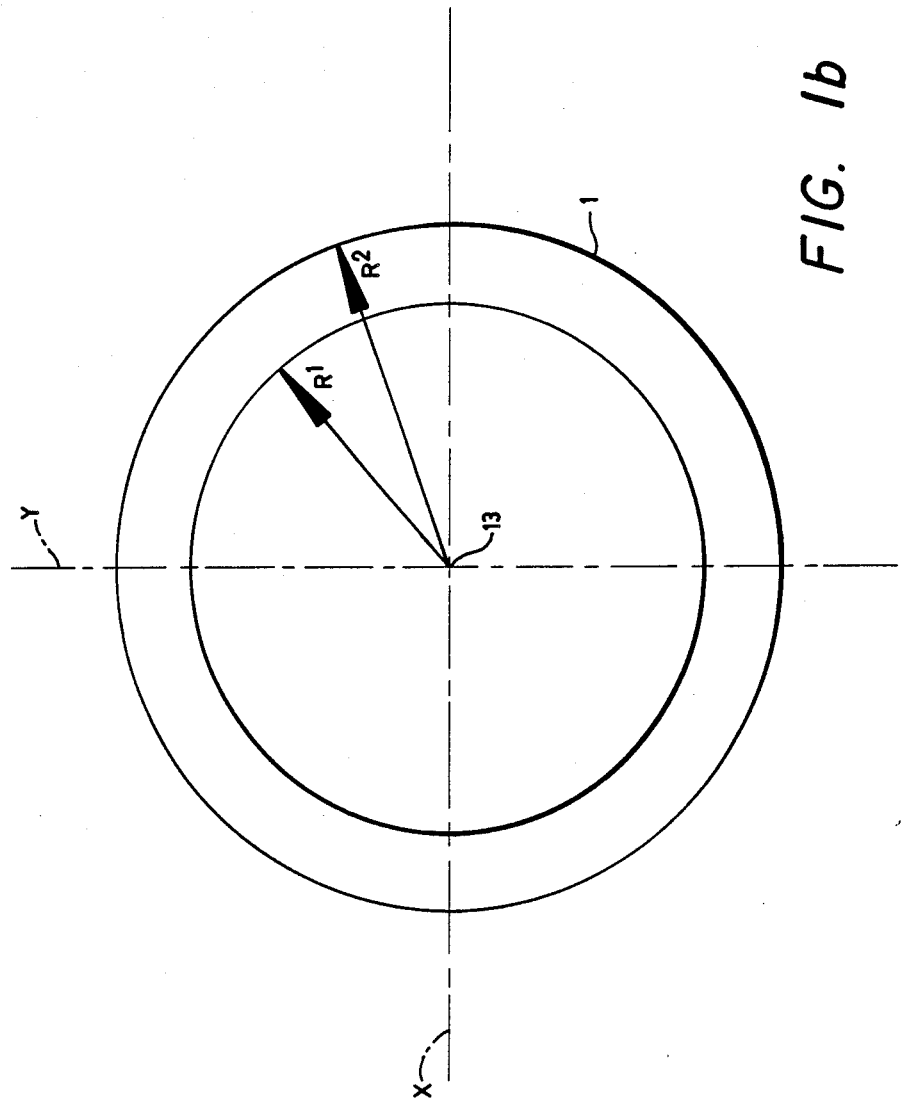

FIG. 1b illustrates a cross-sectional view of the major cylindrical portion 2 of the arc tube shown in FIG. 1a. $R_2$ is the outer radius of the arc tube and $R_1$ is the inner radius of the arc tube. For a typical arc tube, $R_1 = 10$ mm and $R_2 = 11$ mm. The difference between $R_1$ and $R_2$ is the thickness of the arc tube wall. The drawing also illustrates the y-axis of the arc tube.

In FIG. 2 there is schematically shown a top view of an apparatus in accordance with a preferred embodiment of the present invention in cross-section in the x-y plane. The preferred embodiment illustrated is for use in discharge arc tube diagnostics. As shown, the apparatus has positioned therein an article comprising a discharge lamp arc tube. FIG. 2 also illustrates the trajectory of a light beam from a light source through the apparatus and arc tube mounted therein.

In FIG. 2, the x axis is along the optical axis 21, the y axis is perpendicular to x in the plane of the figure, and the z axis is perpendicular to the plane of the paper. The origin of the axis system is at the center of the sample tube 13.

As illustrated, radiation in the form of a single ray 26 travels from right to left. The ray 26 is parallel to, and offset by a distance $y_1$ from, the optical axis 21. (The components of the apparatus 22, 24, 25, 27, and 28 are approximately centered to the optical axis 21.)

At a first point on the optical axis 21 there is provided a first compensating means 22 for refracting light rays from a laser beam light source 23 by an amount equal to the refraction occurring when the light ray passes into the article to form compensated radiation. In the embodiment shown the compensating means comprises a half of a tube which is approximately identical to the cylindrical portion of the sample arc tube. The half tube is obtained by bisecting the approximately identical tube along its longitudinal axis. The first half tube is mounted with its concave (open) side facing the light source with its opposite convex side being closest to the sample tube such that with the plane of bisection u of the half tube is perpendicular to the optical axis 21.

At a second point along the optical axis 21, there is provided first means 24 for inverting the refraction of the compensated radiation. In the drawing, the first inverting means comprises a first cylindrical lens. The location of the first cylindrical lens measured from the primary plane v thereof is a distance $S_1$ along the optical axis 21 from the bisection plane u of the first half tube.

At a third point along the optical axis 21 there is provided a means for releasably holding a sample tube 25. The sample tube 25 is positioned such that the longitudinal axis z of the tube is perpendicular to the light beam 26 emitted from the light source and parallel to the longitudinal axes of the first and second compensating means. The longitudinal axis z of the sample tube is a distance $S_2$ along the optical axis 21 from the primary plane v of the first cylindrical lens.

At a fourth point along the optical axis 21 is located a second means 27 for inverting the refraction of the light ray that passes out of the sample tube. As shown, the second inverting means comprises a second cylindrical lens. (In the drawing the second cylindrical lens is assumed to have a focal length equal to that of the first cylindrical lens.) The location of the second cylindrical lens along the optical axis 21 is such that the primary plane w of the second cylindrical lens is a distance $S_3$ from the center 13 of the sample tube.

At a fifth point along the optical axis 21 is a second compensating means 28 for refracting the inverted refracted light ray by an amount equal to the refraction occurring when radiation passes out of the article such that the light radiation 29 exiting the second compensating means is on approximately the same predetermined path as the light beam first generated by the light source. The second compensating means 28 illustrated in the drawing comprises a half tube. The half tube is prepared from a tube identical to the cylindrical portion of the sample arc tube which has been bisected along its longitudinal axis. The half tube is mounted with its plane of bisection t perpendicular to the optical axis 21. The location of the half tube along the optical axis 21 is such that the plane of bisection t of the second half tube is a distance $S_4$ from the primary plane w of the second cylindrical lens.

When the two cylindrical lenses have the same focal length, as is assumed in FIG. 2, the distances $S_1 = S_2 = S_3 = S_4$, which are equal to two times the focal length of one of the cylindrical lenses. The focal length should be as short as possible to minimize the size of the lenses, but is subject to the constraint that the width of a cylindrical lens, or the diameter of a spherical lens, is usually at least twice the diameter of the sample tube in order to collect strongly refracted rays, and that the focal length is usually longer than the width or diameter of the lens. For example, a lens having a focal length (lens diameter width) of 35 mm would be suitable for use with a typical arc tube having an inside radius ($R_1$) of 10 mm and an outside radius ($R_2$) of 11 mm.

FIG. 2 also shows the trajectory of a light beam from a light source through the apparatus which includes a sample tube mounted therein. The light beam is emitted from the light source on a predetermined path, 26. As the light passes through the first half tube, it is refracted through an angle, $\Delta$, where $$\Delta = \sin^{-1}\left(\frac{y_1}{nR_1}\right) - \sin^{-1}\left(\frac{y_1}{nR_2}\right) +$$

$$\sin^{-1}\left(\frac{y_1}{n'R_2}\right) - \sin^{-1}\left(\frac{y_1}{n'R_1}\right),$$

wherein: $y_1$ represents the displacement of the light beam along the y-axis relative to the optical axis; $R_1$ is the inner radius of the arc tube; $R_2$ is the outer radius of the arc tube; and n' is the refractive index of the arc tube and n is the index of refraction of the medium in the cavity of the article and external to the article. Usually n=1, as for air or vacuum. The refracted beam next passes through the first cylindrical lens which inverts the refraction. The inverted refracted beam then passes through a first wall of the sample tube. The sample tube wall refracts the pre-refracted light beam passing therethrough to effect cancellation of the pre-refraction such that the light passing through the cavity, or inner portion, of the sample tube is on approximately the same predetermined path, 10, as when the light was first emitted from the light source.

When the light passes out of the sample arc tube cavity through the tube wall opposite its point of entry, the light ray is again refracted. The refracted light ray then passes through the second cylindrical lens where the refraction is inverted. The inverted refracted light ray then passes through the second half-tube to effect cancellation of the inverted refraction of the light ray such that the light emerging from the apparatus is on approximately the same predetermined path, 29, as it was in the sample tube cavity 10 and when the light ray was first emitted from the light source 26.

Optionally, a detector 30 can be positioned to receive the radiation that passes out of the apparatus in order to provide a predetermined type of analysis or measurement.

While FIG. 2 illustrates an apparatus in which the components are in a linear arrangement, the components may be arranged in alternative configurations with the use of mirrors and/or other optical components known to those in the art.

Further, while FIG. 2 illustrates an apparatus in which the components have cylindrical symmetry resulting in refraction only in the y direction, the apparatus may alternatively include components with spherical symmetry which may be used to correct for refraction in both the Y and z directions. That alternative apparatus comprises spherical lenses the hemi-spheres cut from an identical copy of the spherically symmetrical sample article. Furthermore, sample articles of arbitrary shape causing either y or z refraction, or both, may be used in conjunction with bisected halves cut from an identical copy of the sample article, along with spherical lenses.

In FIG. 3, there is schematically shown the top view of an apparatus in accordance with a preferred embodiment of the present invention in cross-section in the x-y plane. FIG. 3 schematically shows the first compensating means 22, the first inverting means 24, the sample article 25, the second inverting means 27, and the second compensating means 29. FIG. 3 schematically represents a preferred support means which includes translating mounts 34, 35, 37, and 38 to provide motion along the x and y axes for each item so that each item may be aligned to the article 25 mounted in the holding means 36 by adjusting the focal positions of the lenses and pre-refracting means and post-refracting means and to center each item on the optical axis 21 of the system. The translating mounts 34, 35, 37, and 38 for the optical components 22, 24, 27, and 28 are all mounted to a common translating mount 39 to which the holding means 36 is also mounted, such that the components 22, 24, 25, 27, and 28 of the apparatus can be translated in the y direction as a unit relative the light source 23 and the detector 30, which are both immovably mounted. The translating mounts 34, 35, 37, 38 and 39 may be in platform form, as shown in FIG. 3, or may have any other configuration which is adapted to support and align the element of the apparatus mounted thereon. In a most preferred embodiment, holding means 36 is provided with an electrical socket connected to a power source such that an arc tube enclosed within an outer envelope can be positioned in the holding means 36. This permits a discharge to be created in the arc tube and the discharge to be analyzed using the apparatus of the present invention.

In a more preferred embodiment of the present invention, the apparatus is included within a housing, or enclosure, which is temperature controlled to allow heating or cooling of the contents of the sample tube without misaligning the components due to thermal effects. Such housing is fitted with planar, transparent entrance and exit windows, or ports, to facilitate passage of the light ray(s) therethrough. To prevent refraction effects due to the windows, the windows, which are rendered fixed in space by the apparatus, should be mounted perpendicular to the light rays.

Most preferably, when the housing or enclosure is used, the enclosure is filled with a medium, e.g., a fluid or gas, having a refractive index which matches that of the contents of the sample tube. The filling of the enclosure in this manner is especially beneficial where the refractive index of the sample tube contents varies substantially from the refractive index of air. (The refractive index of air is approximately 1.) For example, if the contents of the sample tube were an aqueous solution the entire apparatus is most preferably submerged in water within the housing.

The apparatus of the present invention is particularly advantageous in laser absorption and scattering experiments. In such applications, the apparatus of the present invention reduces the arc tube aberrations.

In any laser scattering experiment where the detector optics are on the y axis, the apparatus will maintain the alignment of the variably displaced laser beam with the fixed detector optics. Referring to FIG. 2, an apparatus comprising only the first half tube, cylindrical lens, and sample holding means are needed in a laser scattering application.

In a crossed-beam laser scattering or absorption experiment, a second beam traverses the sample tube along the y axis. The apparatus maintains the alignment of the variably-displaced first beam relative to the fixed second beam at a fixed spatial location as the offset, $y_1$, of the first beam is varied. Referring to FIG. 2, an apparatus comprising only the first compensating means, first inverting means, sample holding means is needed in a crossed-beam laser scattering experiment. An apparatus for use in a crossed-beam laser absorption experiment, where the transmission of the first beam to the detector provides the signal, further comprises the second compensating means and second inverting means, as shown in FIG. 2.

In a laser absorption experiment where a linear photodiode array (e.g., OMA) is used as the detector, the y position on the detector corresponds directly to the $y_1$ position of the ray in the arc tube cavity without distortions due to arc tube refraction.

While there have been shown and described what are considered preferred embodiments of the present invention, it will be obvious to those skilled in the art that various changes and modifications may be made therein without departing from the invention as defined by the appended claims.

What is claimed is:

1. An apparatus for use in arc tube discharge diagnostics to compensate for refraction of a laser beam passing through an arc tube, the apparatus comprising:

means for supporting and aligning components of the apparatus;

means for pre-refracting radiation on a predetermined path from a laser source path by an amount equal and inverse to refraction which occurs when radiation passes through a first wall of the arc tube such that when the radiation passes through the first wall of the arc tube and into the cavity thereof the radiation passes through the arc tube cavity on the predetermined path, the pre-refracting means being mounted to the support means;

means for releasably holding the arc tube such that the radiation passes through the arc tube cavity, the holding means being mounted on the support means at a predetermined point relative to the pre-refracting means.

2. An apparatus in accordance with claim 1 further comprising means for post-refracting radiation emerging from a point of the arc tube opposite its point of entry by an amount equal and inverse to refraction which occurs when radiation emerges from the article, the post-refracting means being mounted on the support means at a predetermined point relative to the holding means.

3. An apparatus in accordance with claim 2 wherein the pre-refracting means comprises compensating means for refracting radiation by an amount equal to the refraction caused by the first wall of the arc tube and means for inverting the refraction of the refracted radiation.

4. An apparatus in accordance with claim 3 wherein the post-refracting means comprises means for inverting the refraction of the radiation emerging from the arc and compensating means for refracting radiation by an amount equal to the refraction occurring when radiation emerges from the article.

5. An apparatus in accordance with claim 4 wherein the pre-refracting means, holding means, post-refracting means are within a housing, the housing being temperature controlled to allow heating or cooling of the article.

6. An appratus in accordance with claim 5 wherein the housing is filled with a medium having a refractive index approximately equal to that within the cavity of the arc tube.

7. An apparatus in accordance with claim 2 wherein the means for post-refracting radiation comprises a second half tube comprising a longitudinally bisected tube obtained from a tube which is approximately identical to the arc tube's cylindrical portion and a second cylindrical lens, the second half tube being mounted with its convex side facing the radiation source and the second cylindrical lens being mounted between the arc tube and the second half tube.

8. An apparatus in accordance with claim 1 wherein the means for pre-refracting radiation comprises a first half tube comprising an longitudinally bisected tube obtained from a tube which is approximately identical to the arc tube's cylindrical portion and a first cylindrical lens, the first half tube being mounted with its concave side facing the radiation source and the first cylindrical lens being mounted between the first half tube and the arc tube.

9. A method to compensate for refraction of a laser beam passing through an arc tube in arc tube discharge diagnostics, said method comprising:
  pre-refracting radiation traveling on a predetermined path by an amount approximately equal and inverse to the refraction occurring when the radiation passes through a first wall of the arc tube to form pre-refracted radiation such that when the radiation passes through the first wall of the arc tube and into the cavity thereof the radiation passes through the arc tube cavity on the predetermined path;
  passing the pre-refracted radiation through the first wall of the of the arc tube and into the cavity thereof, the first wall cancelling the pre-refraction such that the radiation passes through the cavity of the article on the predetermined path.

10. A method in accordance with claim 9 further comprising post-refracting the radiation emerging from the arc tube by an amount approximately equal and inverse to the refraction occurring when radiation on a predetermined path passes through a second wall of the arc tube, thereby providing a light output approximately on the predetermined path.

11. A method to compensate for refraction of radiation passing out of an arc tube in arc tube discharge diagnostics, the wall of which arc tube refracts radiation passing therethrough, said method comprising:
  refracting radiation emerging from a wall of the arc tube by an amount approximately equal and inverse to refraction occurring when the radiation passes through the wall out of the arc tube such that the refracting means cancels the refraction of the radiation caused when the radiation passes through the wall of the arc tube.

* * * * *